United States Patent [19]

Hyatt

[11] Patent Number: 5,929,298
[45] Date of Patent: Jul. 27, 1999

[54] PROCESS FOR PREPARING CONJUGATED DIENES USING SUBSTITUTED RHENIUM TRIOXIDE

[75] Inventor: John Anthony Hyatt, Kingsport, Tenn.

[73] Assignee: Eastman Chemical Company, Kingsport, Tenn.

[21] Appl. No.: 09/115,220

[22] Filed: Jul. 13, 1998

[51] Int. Cl.$^6$ .................................. C07C 1/20; C07C 5/09
[52] U.S. Cl. ............................................. 585/609; 585/629
[58] Field of Search .................................. 585/609, 629, 585/606, 627

[56] References Cited

U.S. PATENT DOCUMENTS

| | | | |
|---|---|---|---|
| 2,516,849 | 8/1950 | Brasch | 585/609 |
| 5,349,097 | 9/1994 | Thome et al. | 568/904 |

FOREIGN PATENT DOCUMENTS

| | | | |
|---|---|---|---|
| 577364 | 5/1946 | United Kingdom | 585/609 |

OTHER PUBLICATIONS

Herrmann et al, Journal of Molecular Catalysis, 86, 243–266, (1994).
Rudolph et al, J. Am Chem Soc. 119, 6189–6190 (1997).
Zhu et al, Journel of Molecular Catalysis A: Chemical 103, 87–94 (1995).
Herrmann et al, Angew. Chem. Int. Ed. Engl. 30, 1636 (1991).
Zhu et al, J. Org. Chem., 61, 324–328 (1996).
Bartlett et al, J. Am. Chem. Soc. 90, 2049 (1968).
Quin et al, Heterocyclic Chem. 19, No. 5, 1041–1044 (1982).
Herz et al, J. Org. Chem. 50, 618–627, (1985).
Markgraf et al, Synthetic Communications 14(7), 647–653 (1984).
Paquette et al, Tetrahedron Letters, No. 45, 4033–4036 (1976).
Adams et al, Organic Reactions, vol. IV, John Wiley and Sons, New York, pp. 1–170 (1949).
Markgraf et al, Tetrahedron Letters, vol. 24, No. 3, pp. 241–244.
Backer, Rec. Trav. Chim. 62, 564–568 (1943).

*Primary Examiner*—Glenn Caldarola
*Assistant Examiner*—In Suk Bullock
*Attorney, Agent, or Firm*—Bernard J. Graves, Jr.; Matthew W. Smith; Harry J. Gwinnell

[57] ABSTRACT

This invention provides a process for preparing conjugated dienes using certain substituted rhenium compounds as catalysts. The substituted rhenium compounds have the formula $R_5ReO_3$, wherein $R_5$ is selected from the group consisting of $C_1$–$C_{10}$ alkyl, aryl, aryl-$C_1$–$C_{10}$ alkyl, cyclopentadienyl and cyclopentadienyl substituted with one to four $C_1$–$C_4$ alkyl groups. The process of the invention thus provides a facile method for preparing conjugated dienes using the corresponding tertiary vinyl alcohol as starting material. Examples of such starting materials includes phytols, manool, 5-vinyl-5-nonanol, 1-vinyl4-tert-butylcyclohexanol, and 1-vinylcyclooctanol. The process can be carried out neat as well as in an inert solvent in the gas or solution phase.

9 Claims, No Drawings

PROCESS FOR PREPARING CONJUGATED DIENES USING SUBSTITUTED RHENIUM TRIOXIDE

FIELD OF THE INVENTION

This invention belongs to the field of synthetic organic chemistry. In particular, this invention relates to a process for preparing conjugated dienes using certain substituted rhenium compounds.

BACKGROUND OF THE INVENTION

Substituted rhenium trioxides, particularly methylrhenium trioxide ($CH_3ReO_3$, MTO) have been used for a variety of organic transformations. For example, MTO has been used for the epoxidation of olefins and their deoxygenation, olefin metathesis and rearrangement of allylic alcohols. (See Herrmann, W.; Fischer, R.; Rauch, M.; Scherer, W. *J. Mol. Catal.* 86, 243 (1994); Rudolph, J.; Laxma Reddy, K.; Chiang, J.; Sharpless, K. *J. Am. Chem. Soc.* 119. 6189 (1997),; Zhu, Z.; Espenson, J. *J. Mol. Catal. A: Chemical* 103, 87 (1995); Hermann, W.; Wagner, W.; Flessner, U.; Volkhardt, U.; Komber, H. *Angew. Chem. Int. Ed. Eng.* 30, 1636 (1991); and U.S. Pat. No. 5,349,097.) In U.S. Pat. No. 5,349,097, the following reaction is carried out using methylrhenium trioxide on a secondary vinyl carbinol (Example I):

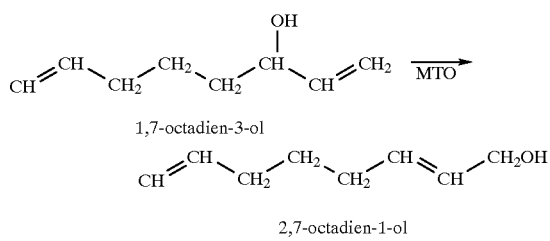

1,7-octadien-3-ol 2,7-octadien-1-ol

The rearranged product, 2,7-octadien-1-ol, is produced with a selectivity of 100%. This would indicate that a secondary vinyl carbinol rearranges readily to form the corresponding allylic alcohol. No examples are used to teach that dehydration to the diene is an accompanying or alternative reaction. In contrast, the tertiary vinyl alcohols used in the present invention, as described below, yield unexpectedly the diene instead of being rearranged to the corresponding allylic alcohol.

Recently, Zhu and Espenson *J. Org. Chem.*, 61, 324–328 (1996), have reported that MTO catalyzes the formation of symmetrical ethers from primary aliphatic alcohols and unsymmetrical ethers from two different alcohols and the dehydration of alcohols to form olefins; however, the dehydration reaction reportedly required long reaction times and no vinyl carbinols are dehydrated to produce dienes.

The present invention, as described below, shows that certain tertiary vinyl carbinols can be dehydrated conveniently to produce substituted 1,3-butadienes in high yields and with good purity by contacting with substituted rhenium trioxides as catalysts, particularly methyl rhenium trioxide.

This dehydration of tertiary vinyl carbinols to give substituted 1,3-butadienes has traditionally been done by catalysts such as p-toluenesulfonic acid, phosphorous oxychloride in pyridine, molecular sieves, and iodine. (See, Zhu, Z.; Espenson, J., *J. Org. Chem.* 61, 324–328 (1996); Bartlett, P., et al., *J. Am. Chem. Soc.* 90, 2049 (1968); Quin. L. D., et al., *J. Heterocyclic. Chem.* 19, No. 5, 1041–44 (1982), Herz, W. and Juo, R., *J. Org. Chem.* 50, 618–627 (1985); Markgraf. J. H., et al., *Synthetic Communications* 14(7), 647–653 (1984); and Paquette, L. A., et al., *Tetrahedron Lettters, No.* 45, 4033–4036 (1976).) Some of these methods have the disadvantages of requiring long reaction times, producing unwanted by-products or having wastes difficult to dispose of, in contrast to the process of this invention.

SUMMARY OF THE INVENTION

This invention provides a process for preparing conjugated dienes using certain substituted rhenium compounds as catalysts. The substituted rhenium compounds have the formula $R_5ReO_3$, wherein $R_5$ is selected from the group consisting of $C_1$–$C_{10}$ alkyl, aryl, aryl -$C_1$–$C_{10}$ alkyl, cyclopentadienyl and cyclopentadienyl substituted with one to four $C_1$–$C_4$ alkyl groups; however, it is highly preferred that $R_5$ represent a methyl group to denote methylrhenium trioxide (MTO). The process of the invention thus provides a facile method for preparing conjugated dienes using the corresponding tertiary alcohol as starting material. Examples of such starting materials includes phytols, manool, 5-vinyl-5-nonanol, 1-vinyl-4-tert-butylcyclohexanol, and 1-vinylcyclooctanol.

DETAILED DESCRIPTION OF THE INVENTION

This invention provides a process for preparing 1,3-butadienes which comprises contacting a tertiary vinyl carbinol with a at least one substituted rhenium trioxide having the formula $R_5ReO_3$, wherein $R_5$ is a group selected from $C_1$–$C_{10}$ alkyl, aryl, aryl- $C_1$–$C_{10}$ alkyl, cyclopentadienyl, or cyclopentadienyl substituted with one to five $C_1$–$C_4$ alkyl groups.

This invention further provides a process for preparing substituted 1,3-butadienes of the formula

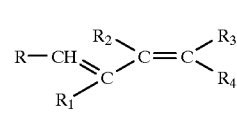

(I)

wherein R is selected from hydrogen, $C_1$–$C_{20}$ alkyl, $C_3$–$C_8$ cycloalkyl, $C_1$–$C_{20}$ substituted alkyl, or substituted $C_3$–$C_8$ cycloalkyl; $R_1$ is selected from $C_1$–$C_{20}$ alkyl, $C_3$–$C_8$ cycloalkyl, $C_1$–$C_{20}$ substituted alkyl or substituted $C_3$–$C_8$ cycloalkyl; or R and $R_1$ may be combined to form a carbocyclic ring containing three to fourteen carbon atoms; and $R_2$, $R_3$, and $R_4$ are independently selected from hydrogen, $C_1$–$C_4$ alkyl, substituted $C_1$–$C_4$ alkyl; $C_3$–$C_8$ cycloalkyl, substituted $C_3$–$C_8$ cycloalkyl, aryl or substituted aryl; which comprises contacting a compound of formula (II):

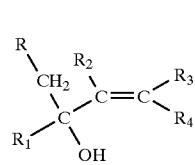

(II)

with at least one substituted rhenium trioxide having the formula $R_5ReO_3$, wherein $R_5$ is a group selected from $C_1$–$C_{10}$ alkyl, aryl, aryl-$C_1$–$C_{10}$ alkyl, cyclopentadienyl, or cyclopentadienyl substituted with one to five $C_1$–$C_4$ alkyl groups.

The terms "$C_1$–$C_4$ alkyl", "$C_1$–$C_{10}$ alkyl", and "$C_1$–$C_{20}$ alkyl" are used to describe fully saturated hydrocarbon radicals containing one to four, one to ten, and one to twenty carbon atoms, respectively, having straight or branched carbon chains.

The term "aryl" preferably denotes a group selected from phenyl, naphthyl, phenanthryl, anthracenyl, biphenyl, and such groups fused with a heterocyclic ring. Such heterocyclic rings are generally five-membered or six membered rings that have 1 to 4 heteroatoms, such as oxygen, sulfur, and/or nitrogen. Examples of such heterocyclic rings include thienyl, furyl, pyrrolyl, imidazolyl, pyrazolyl, thiadiazolyl, oxadiazolyl, tetrazolyl, thiatriazolyl, oxatriazolyle, pyridyl, pyrimidyl, pyrazinyl, pyradazinyl, thiazinyl, oxazinyl, thriazinyl, thiadiazinyl, imidazolinyl, dihydropyrimidinyl, tetrahydropyrimidinyl, tetrazolo[1,5-b]pyridazinyl, and purinyl. The term "subsititued aryl" denotes an aryl group substituted with one or more groups selected from $C_1$–$C_4$ alkyl and $C_3$–$C_8$ cycloalkyl.

The term "$C_3$–$C_8$ cycloalkyl" is used to describe a cyclic hydrocarbon radical containing three to eight carbon atoms and these radicals substituted with one or more groups selected from $C_1$–$C_4$ alkyl and aryl.

The term "$C_1$–$C_{20}$ substituted alkyl" preferably denotes a $C_1$–$C_{20}$ alkyl group substituted one to four times with a group which does not interfere with the elimination reaction of the invention. Examples of such groups include $C_1$–$C_6$ alkoxy, $C_1$–$C_6$ alkanoyloxy, $C_3$–$C_8$ cycloalkyl, aryl, $C_1$–$C_6$ alkoxycarbonyl, $C_1$–$C_6$ alkyl-C(O)-$C_1$–$C_6$ alkyl, $C_2$–$C_7$ alkenyl, $C_2$–$C_7$ alkynyl, and the like. Likewise, terms such as "substituted $C_3$–$C_8$ cycloalkyl" and "substituted aryl" denote such cycloalkyl and aryl groups substituted one to four times with a groups which does not interfere with the elimination reaction of the invention.

The term "$C_2$–$C_7$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains. Allyl and 3-butene-1-yl are preferred embodiments.

The term "$C_2$–$C_7$ alkynyl" denotes such radicals as ethynyl, propynyl, butynyl, pentynyl, hexynyl, heptynyl, as well as di- and tri-ynes.

When R and $R_1$ are combined to produce a carbocyclic ring the ring may be fully saturated or contain one or more double bonds and contain from three to fourteen carbon atoms. Further, the carbocyclic ring may contain one or more substituents selected from $C_1$–$C_4$ alkyl, $C_3$–$C_8$ cycloalkyl and aryl. Alternatively, the carbocyclic ring may contain other carbocyclic rings such as $C_3$–$C_8$ cycloalkyl-1,2-diyl or arylene group to produce rings such as:

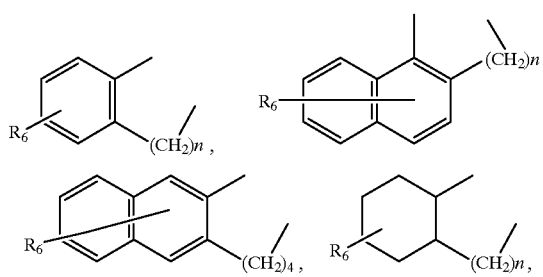

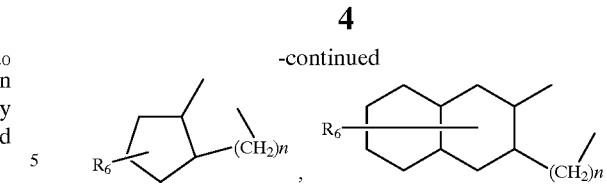

and the like, wherein n is one to four, and $R_6$ is hydrogen or one or more groups selected from $C_1$–$C_4$ alkyl and aryl. Further, the carbocyclic ring may contain one or more hetero atom selected from oxygen, sulfur and nitrogen to produce rings such as:

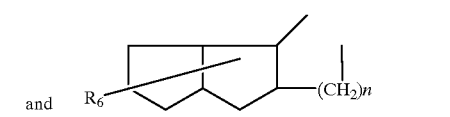

and the like.

The term "arylene" is used to denote a divalent aromatic radical selected from 1,2-phenylene, naphthalene-1,2-diyl and naphthalene-2,3-diyl and these substituted with one or more groups selected from $C_1$–$C_{12}$ alkyl, $C_3$–$C_8$ cyclo alkyl or aryl.

The term $C_3$–$C_8$ cycloalkane-1,2-diyl is used to describe cycloalkane-1,2-diyl radicals containing three to eight carbon atoms and these substituted with one or more $C_1$–$C_4$ alkyl groups.

The term "aryl- $C_1$–$C_{10}$ alkyl," is used to describe monovalent radicals having, in the case of straight chain alkyl groups, the structure aryl-$(CH2)_m$, wherein m=1 to 10.

It has been determined that the dehydration reaction produces many unwanted by-products when one or both of R and $R_1$ in the starting vinyl carbinol are hydrogen; thus only tertiary vinyl carbinols appear to useful within the scope of the invention (Comparative Example 2).

The starting vinyl carbinols II are available commercially or may be easily prepared by reacting the appropriate ketones A with

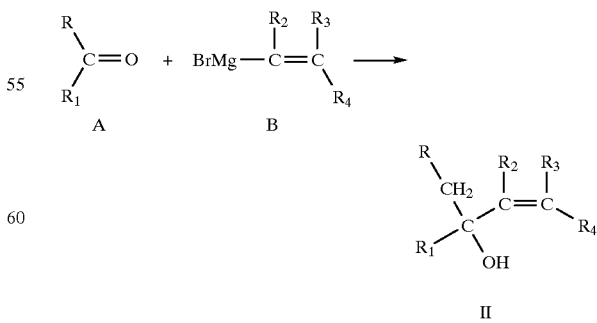

the vinylmagnesium bromides B in ethers such as tetrahydrofuran.

Certain substituted 1,3-butadienes prepared by the process of the invention are useful to react with dienophiles in the Diels-Alder reaction to provide many classes of useful organic chemicals including carboxylic acids, dicarboxylic acids, anhydrides, aldehydes, substituted quinones, esters, halides, ketones, nitriles, sulfones, etc. (See, for example, Bartlett, P., et al., *J. Am. Chem. Soc.* 90, 2049 (1968); Adams, R. et al., editors, *Organic Reactions,* Vol. IV, John Wiley and Sons, New York, pp. 1–170 (1949); Markgraf, J. H., et al., *Tetrahedron Letters,* Vol. 24, No. 3, pp. 241–244 (1983); and Backer, H.; van der Brij, *Rec. Trav. Chim.* 62, 564–568 (1943)).

A wide variety of tertiary vinyl carbinols, for example, those having formula II

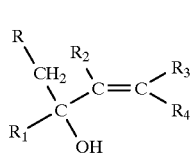

(II)

can be used in the practice of the invention; however, it is highly preferred that $R_2$, $R_3$, and $R_4$ represent hydrogen atoms.

The useful substituted rhenium trioxides have the formula $R_5ReO_3$, wherein $R_5$ is selected from the group consisting of $C_1$–$C_{10}$ alkyl, aryl, aryl-$C_1$–$C_{10}$ alkyl, cyclopentadienyl and cyclopentadienyl substituted with one to four $C_1$–$C_4$ alkyl groups; however, it is highly preferred that $R_5$ represent a methyl group to denote methylrhenium trioxide (MTO).

The reaction can be carried out over a wide temperature range, and is preferably done at temperatures from about 25° C. to 250° C. The substituted rhenium trioxide catalyst is preferably used at a level of about 0.01–10.0% by weight based on the weight of the starting tertiary vinyl carbinol, and is most preferably used at level of 0.05 to 5.0% by weight.

The reaction may be carried out neat or in the presence of an inert solvent including aromatic hydrocarbons, aliphatic hydrocarbons, cycloaliphatic hydrocarbons, aliphatic esters, ethers, carboxamides, sulfoxides, ketones, etc. Typical aliphatic hydrocarbons include straight or branched chain alkanes having five to eight carbon atoms, particularly n-heptane. Useful aromatic hydrocarbons include benzene and benzene substituted with one to three $C_1$–$C_4$ alkyl groups, with toluene and xylenes being the most preferred. The most useful aliphatic esters have three to nine carbons and have the formula $R_8CO_2R_7$, wherein $R_7$ and $R_8$ independently represent a straight or branched chain $C_1$–$C_4$ alkyl group, with ethyl acetate being the preferred aliphatic ester. The term "ether" is used to include compounds having the formulas $R_7$—O—$R_8$, $R_7$—O($CH_2CH_2O)_{1-3}$—$R_8$, wherein $R_7$ and R8 are as defined above, and tetrahydrofuran, with tetrahydrofuran being the preferred ether solvent. Typical polar aprotic amide solvents include N,N-dimethylformamide, N,N-dimethylacetamide and N-methyl-2-pyrrolidinone. Typical sulfone solvents include dimethyl sulfone and sulfolane. Typical useful cycloaliphatic hydrocarbons are $C_5$–$C_8$ cycloalkanes and these substituted with one or more $C_1$–$C_4$ alkyl groups, e.g., cyclohexene, cyclohexane, methyl cyclohexane and cycloheptane.

The process may be carried out in the vapor phase. The process may be carried out in the presence or in an inert atmosphere of inert gas such as argon or nitrogen and may be done under normal atmospheric pressure or at elevated or reduced pressure if desired or convenient.

The following examples illustrate further the practice of the invention.

Example 1 - Phytadienes from Isophytol

A mixture of 1.0 g isophytol, 12 ml of benzene, and 25 mg of methylrhenium trioxide was stirred at reflux. After 30 minutes, VPC analysis indicated about 50% conversion to a mixture of the three isomeric phytadienes. Reflux was continued to about 20 hours total. The reaction mixture was cooled, filtered through a pad of silica gel to remove catalyst, and stripped of volatiles on the vacuum line to leave 0.93 gram (99%) of a mixture of phytadiene isomers. No phytol, isophytol, or other contaminants were detected by VPC or NMR analyses.

Example 2 - Phytadienes from Phytol

A solution of 5.0 grams of phytol (cis/trans mixture), 50 ml of benzene, and 50 mg of methylrhenium trioxide was stirred under reflux. VPC analysis at 15 minutes reaction time showed that most of the phytol had been converted to isophytol, and about 35% conversion to a mixture of isomeric phytadienes had occurred. After 30 minutes, almost no phytol remained, the mixture consisting of about equal parts of isophytol and phytadienes. The reaction was continued for a total of 7 hour, cooled, filtered through a silica gel pad to remove catalyst, and stripped of volatiles under vacuum to give 4.6 grams (97%) of phytadienes as a pale yellow liquid. Distillation gave 4.40 grams (90%) colorless phytadienes, bp 95–140 deg C./0.1 mm Hg. VPC and NMR analysis showed the product mixture to consist of the same three phytadienes in the same proportion as was obtained from isophytol (vide supra).

Example 3 - Dehydration of Vinylcyclododecanol

A solution of 1.20 grams of 1-vinylcyclododecanol, 10 ml of toluene, and 20 mg of methylrhenium trioxide was refluxed 4 hrs, by which time VPC and TLC analyses indicated complete consumption of the starting material. The mixture was cooled, washed with 5% aqueous sodium carbonate solution to remove catalyst, and the organic phase dried (magnesium sulfate) and stripped of volatiles at reduced pressure. There was obtained 1.02 gram (93%) of 1-vinylcyclododecene as ca. 2:1 trans:cis mixture (VPC); NMR spectrum was in good agreement with that expected for the product.

Example 4 - Dehydration of Manool

A solution of 1.5 grams of manool, 20 ml of toluene, and 31 mg of MTO was heated under reflux until no starting material remained (TLC). The solution was cooled, washed with aq. 5% potassium carbonate, dried, stripped, and the oily residue chromatographed on silica gel (hexane elution) to give 0.90 g (64%) of a mixture of the three isomeric manool dehydration products. NMR spectrum was consistent with this structure assignment.

Example 5 - Dehydration of 5-Vinyl-5-nonanol

A solution of 5.1 grams of 5-vinyl-5-nonanol in 25 ml of toluene containing 38 mg of MTO was refluxed overnight, cooled, washed with aq. potassium carbonate, dried, stripped, and the residue distilled at 25 mm Hg to give 2.55 g (56%) of 5-vinyl-4-nonene as a cis/trans mixture, identified by NMR spectroscopy.

Example 6 - Dehydration of 1-Vinyl-4-tert-butylcyclohexanol

A solution of 2.0 grams of 1-vinyl-4-tert-butylcyclohexanol in 30 ml of toluene containing 40 mg of MTO was refluxed 4 hrs. TLC analysis indicated the presence of some residual starting material, so an additional 10 mg of MTO was added and reflux continued until the starting material was consumed. Workup as in the case of 5-vinyl-5-nonanol above gave 1.25 g (69%) of product as a colorless liquid, bp 90 deg C./15 mm Hg. NMR spectrum was consistent with that expected for the product.

Example 7 - Dehydration of 1-Vinyl-benzocycloheptan-1-ol

Dehydration of 3.0 grams of the title compound with 40 mg of MTO in 20 ml of toluene followed by workup as described in Example 6 afforded after distillation 1.39 grams of 1-vinylbenzocycloheptene, bp 106–115 deg C/8 mm Hg.

Example 8 - Dehydration of 1-Vinylcyclooctanol

A solution of 6 grams of 1-vinylcyclooctanol and 50 mg of MTO in 30 ml of benzene was refluxed 18 hours, cooled, washed with aq. potassium carbonate, dried, stripped of solvent and distilled (82–85 deg C./25 mm Hg) to give 3.55 grams of 1-vinylcyclooctene judged to be of 95% purity of NMR analysis; the only impurity was cyclooctanone left over from preparation of the vinyl carbinol.

Comparative Example 1 - Dehydration of Isophytol Using p-Toluenesulfonic Acid Catalyst A mixture of 1 gram isophytol, 7 ml of toluene, and 10 mg of p-toluenesulfonic acid was stirred under reflux for 0.5 hour, at which time TLC analysis showed complete conversion of isophytol to non-polar products. VPC analysis showed the absence of isophytol and phytol, and the formation of seven distinct product peaks, three of which are the three phytadienes obtained from isophytol with MTO. This is in contrast to the process of this invention where only the three expected phytadiene isomers are formed (Example 1).

Comparative Example 2 - Attempted Dehydration of a Secondary Vinyl Carbinol (1decene-3-o1)

A solution of 5.0 grams of 1-decen-3-o1 and 33 mg of MTO in 40 ml of toluene was refluxed overnight. TLC analysis indicated the presence of much unchanged starting alcohol. An additional 33 mg of MTO was added and reflux continued 8 hrs. Workup by the usual methods described above gave an oily product shown by VPC and NMR to consist of a large number of products. Pure 1,3-decadiene was not recoverable from the mixture. This example shows that the invention is not useful for the dehydration of secondary vinyl carbinols to produce 1,3-butadienes in good yield and purity.

I claim:

1. A process for preparing 1,3-butadienes which comprises contacting a tertiary vinyl carbinol with a at least one substituted rhenium trioxide having the formula $R_5ReO_3$, wherein $R_5$ is a group selected from $C_1$–$C_{10}$ alkyl, aryl, aryl-$C_1$–$C_{10}$ alkyl, cyclopentadienyl, or cyclopentadienyl substituted with one to five $C_1$–$C_4$ alkyl groups.

2. A process for preparing substituted 1,3-butadienes of the formula

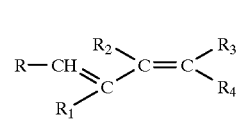

(I)

wherein R is selected from hydrogen, $C_1$–$C_{20}$ alkyl, $C_3$–C8 cycloalkyl, $C_1$–$C_{20}$ substituted alkyl, or substituted $C_3$–$C_8$ cycloalkyl; $R_1$ is selected from $C_1$–$C_{20}$ alkyl, $C_3$–$C_8$ cycloalkyl, $C_1$–$C_{20}$ substituted alkyl or substituted $C_3$–$C_8$ cycloalkyl; or R and $R_1$ may be combined to form a carbocyclic ring containing three to fourteen carbon atoms; and $R_2$, $R_3$, and $R_4$ are independently selected from hydrogen, $C_1$–$C_4$ alkyl, substituted $C_1$–$C_4$ alkyl; $C_3$–$C_8$ cycloalkyl, substituted $C_3$–$C_8$ cycloalkyl, aryl or substituted aryl; which comprises contacting a compound of formula (II):

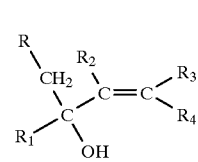

(II)

with at least one substituted rhenium trioxide having the formula $R_5ReO_3$, wherein $R_5$ is a group selected from $C_1$–$C_{10}$ alkyl, aryl, aryl-$C_1$–$C_{10}$ alkyl, cyclopentadienyl, or cyclopentadienyl substituted with one to five $C_1$–$C_4$ alkyl groups.

3. The process of claim 2, wherein $R_5$ is methyl.

4. The process of claim 2, wherein R and $R_1$ are $C_1$–$C_{20}$ alkyl.

5. The process of claim 2, wherein $R_2$, $R_3$, and $R_4$ are hydrogen.

6. The process of claim 2, wherein said process is carried out in an inert solvent.

7. The process of claim 2, wherein said process is carried out in the vapor phase.

8. The process of claim 2, wherein said process is carried out at a temperature of about 25° C. to 250° C.

9. The process of claim 2, wherein said substituted rhenium trioxide is present at a level of about 0.01 to 10% by weight, based on the weight of the compound of formula I.

* * * * *